US008992783B2

(12) United States Patent
Lorenz et al.

(10) Patent No.: US 8,992,783 B2
(45) Date of Patent: Mar. 31, 2015

(54) PROCESS FOR ENANTIOSEPARATION OF CHIRAL SYSTEMS WITH COMPOUND FORMATION USING TWO SUBSEQUENT CRYSTALLIZATION STEPS

(75) Inventors: Heike Lorenz, Magdeburg (DE); Henning Kaemmerer, Magdeburg (DE); Daniel Polenske, Egeln (DE); Andreas Seidel-Morgenstern, Magdeburg (DE)

(73) Assignee: Max-Planck-Gessellschaft zur Förderung der Wissenschaften e.V., München (DE)

( * ) Notice: Subject to any disclaimer, the term of this patent is extended or adjusted under 35 U.S.C. 154(b) by 816 days.

(21) Appl. No.: 13/062,470

(22) PCT Filed: Jun. 18, 2009

(86) PCT No.: PCT/EP2009/057562
§ 371 (c)(1),
(2), (4) Date: Jun. 23, 2011

(87) PCT Pub. No.: WO2010/025968
PCT Pub. Date: Mar. 11, 2010

(65) Prior Publication Data
US 2011/0263896 A1 Oct. 27, 2011

(30) Foreign Application Priority Data
Sep. 5, 2008 (EP) ..................................... 08163733

(51) Int. Cl.
| B01D 37/00 | (2006.01) |
| B03D 3/06 | (2006.01) |
| B01D 11/02 | (2006.01) |
| B01D 35/18 | (2006.01) |
| B01D 21/00 | (2006.01) |
| C07C 319/28 | (2006.01) |
| B01D 9/00 | (2006.01) |
| C07B 57/00 | (2006.01) |
| C07C 227/34 | (2006.01) |
| C07C 227/42 | (2006.01) |

(52) U.S. Cl.
CPC .............. C07C 319/28 (2013.01); B01D 9/00 (2013.01); C07B 57/00 (2013.01); C07C 227/34 (2013.01); C07C 227/42 (2013.01); C07B 2200/07 (2013.01)
USPC ........... 210/806; 210/696; 210/773; 210/774; 210/714; 562/402; 562/554

(58) Field of Classification Search
CPC .................................. C07B 57/00; B01D 9/04
USPC ............. 62/123; 562/402, 554; 210/696, 773, 210/774, 806, 714
See application file for complete search history.

(56) References Cited

U.S. PATENT DOCUMENTS

| 5,260,482 A | 11/1993 | Pringle et al. |
| 7,820,860 B2 | 10/2010 | Seidel-Morgenstern et al. |
| 2004/0198778 A1 | 10/2004 | Kreft et al. |
| 2008/0207944 A1 | 8/2008 | Seidel-Morgenstern et al. |

FOREIGN PATENT DOCUMENTS

| DE | 19536827 | 4/1997 |
| EP | 0220435 | 5/1987 |
| EP | 0694514 | 1/1996 |
| JP | 60202853 | 10/1985 |
| JP | 200063350 | 2/2000 |
| WO | 9508522 | 3/1995 |
| WO | 97-41084 | 11/1997 |
| WO | 0142173 | 6/2001 |
| WO | 03097582 | 11/2003 |
| WO | 2007023129 | 3/2007 |

OTHER PUBLICATIONS

Chen et al. Purification of Partially Resolved Enantiomeric Mixtures with the Guidance of Ternary Phase Diagram, Organic Process Research and Development, 12, 271-281 (2008).*
Wang et al., "Eutectic Composition of a Chiral Mixture Containing a Racemic Compound," Organic Process Research & Development, 9, 670-676, 2005.*
Polenske, D., et al. (2006) Alternative Einsatzmoglichkeiten der "Bevorzugten Kristallisation" zur Enantiomerentrennung. Chemie Ingenieur Technik, 78(8):1101-10.
Elsner, M., et al. (2005) Experimental Study and Simplified Mathematical Description of Preferential Crystallization. Chirality, 17:S183-95.
Perlberg, A., et al. (2005) Crystal Growth Kinetics via Isothermal Seeded Batch Crystallization: Evaluation of Measurement Techniques and Application to Madelic Acid in Water. Ind. Eng. Chem. Res., 44(4):1012-20.

(Continued)

*Primary Examiner* — Paul A Zucker
*Assistant Examiner* — Mark Luderer
(74) *Attorney, Agent, or Firm* — Lowe Graham Jones PLLC

(57) ABSTRACT

Method for enantioseparation of a chiral system with compound formation comprising a pair of enantiomers. The method comprises the steps of: placing the chiral system to be processed, which is optically enriched by a target enantiomer, in the 3-phase region of the ternary phase diagram of chiral compound forming systems to achieve the establishment of the solid/liquid phase equilibria; phase-separating the liquid and solid phase formed by the placing step; shifting the eutectic composition of the remaining liquid towards a lower eutectic composition ($x_E$) until the overall composition is located in the 2-phase region of the ternary phase diagram of chiral compound forming systems; and performing crystallization in the 2-phase region of the ternary phase diagram for obtaining the target enantiomer in the solid phase. In some cases the shifting step can be skipped.

17 Claims, 3 Drawing Sheets

(56) References Cited

OTHER PUBLICATIONS

Figure 1:
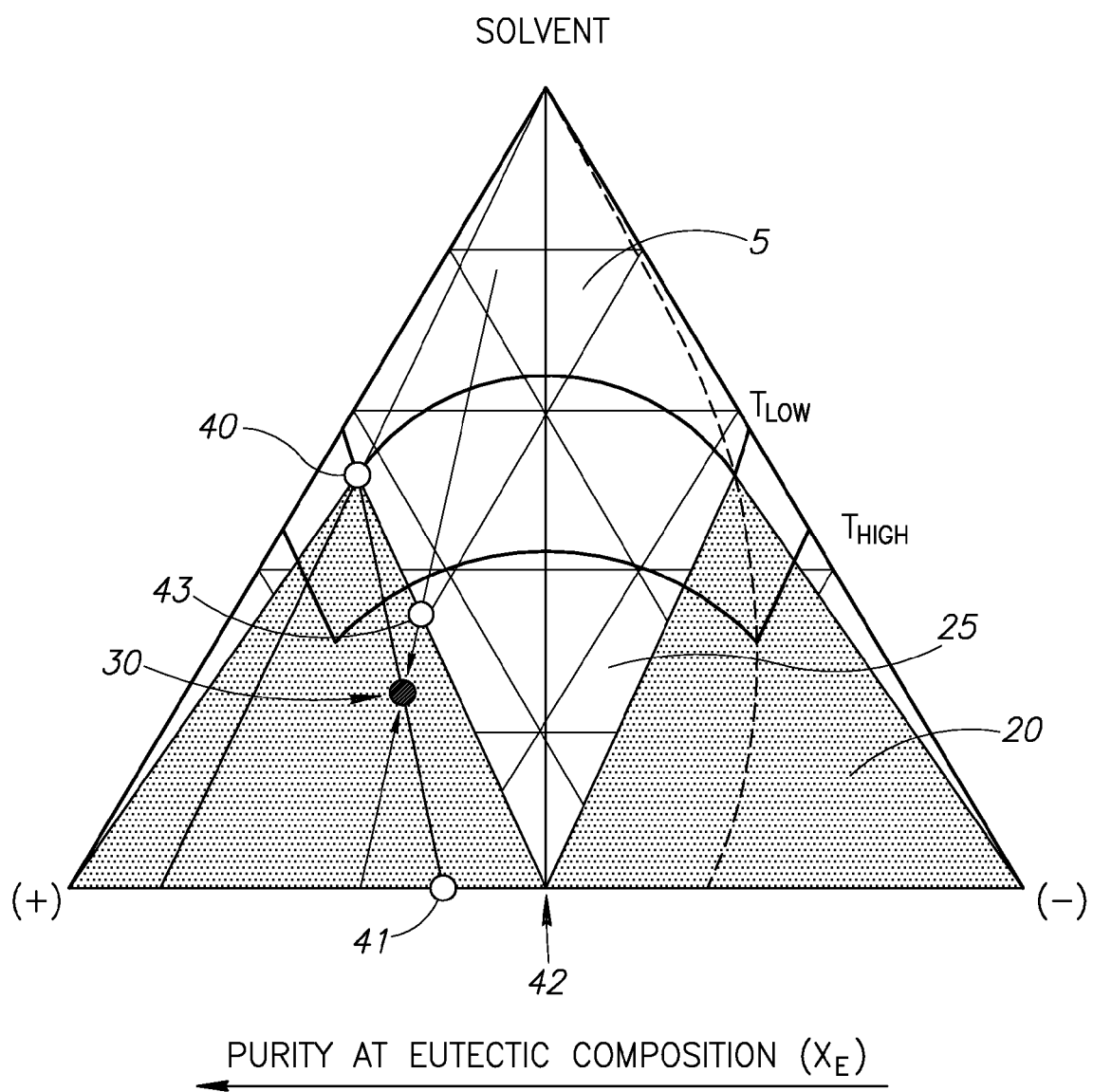

Lorenz, H., et al. (2002) Enantiomeric Mandelic Acid System-Melting Point Phase Diagram and Solubility in Water. J. Chem. Eng. Data, 47(5):1280-84.

Rodrigo, A., et al. (2004) Online Monitoring of Preferential Crystallization of Enantiomers. Chirality, 16:499-508.

van der Ent, E.M., et al. (2001) Design criteria for dense permeation-selective membranes for enantiomer separations. Journal of Membrane Science, 185:207-21.

Sheehan, P., et al. (2000) On Coupling Chromatography and Crystallization to the Separation of Enantiomers; Chemie Ingenieur Technick (72) Chemical Engineer Technology, Life Sciences, 3 pages.

Grandeury, A., et al. (2003) Crystallization of Supramolecular Complexes as an Alternative Route for the Separation of Racemic p-X-Phenylethanol. Chem. Eng. Technol, 26(3):354-58.

"Pharmaceuticals, Chiral" in Kirk Othmer Encyclopedia of Chemical Technology, Copyright 1996 by John Wiley & Sons, Inc., Article Online Posting Date: Dec. 4, 2000, pp. 1-49.

Lorenz, H., et al. (2001) Theoretical and Experimental Study of Thermodynamic and Kinetic Aspetcs of Enantioselective Crystallization. Chemie Ingenieur Technik, 73(6):712.

* cited by examiner

PROCESS FOR ENANTIOSEPARATION OF CHIRAL SYSTEMS WITH COMPOUND FORMATION USING TWO SUBSEQUENT CRYSTALLIZATION STEPS

PRIORITY CLAIM

This is a 371 national phase application based on PCT Application Serial No. EP2009/057562 filed Jun. 18, 2009, which claims priority to European Application Serial No. EP08163733.2 filed Sep. 5, 2008, the contents of which are incorporated herein.

FIELD OF INVENTION

The present invention relates to a method for separation of racemates and in particular a method for enantioseparation of a chiral system with compound formation.

A racemate is an equimolar mixture of two enantiomers. Enantiomers are isomers, i.e. substances which differ from each other only in the arrangement of the atoms but not in the sum formula. Enantiomers show chirality, i.e. they have the properties of image and mirror image or hand and opposite hand. Usually, the two enantiomers are referred to as L-enantiomer and D-enantiomer or (S)- and (R)-enantiomers.

More than half of pharmaceutical active substances are chiral. However, often only one of the two enantiomers can be used as active substance, since both different enantiomers usually have a different physiological effect on the human organism. Besides this, obtaining pure enantiomers is very important in the agricultural chemistry and the food industry. The market for substances of pure enantiomers (for example in pharmaceutical agents, plant protecting agents, dyes and fragrances) has substantially risen in the last years.

A separation of such racemates is usually difficult, since the chemical and physical properties except for the behaviour to linear polarized light and other chiral substances is identical. Herein, only 5 to 10% of all chiral systems are conglomerate forming systems which can be separated by preferential crystallization without prior enrichment by the target enantiomer due to thermodynamic reasons. However, the majority (more than 90%) of all chiral substances, are compound forming systems which cannot be separated. Thus, a lot of effort has been made to provide efficient methods for separation of racemic forming systems. Such a method of the state of the art is known from DE 10 2005 039 501 A1 and WO2007/023129 A2, for example.

However, such methods usually require an initial enantiomeric enrichment of the racemic solution in the order of the eutectic composition of the considered chiral system to yield in a further method step the target enantiomer and/or the racemate from enriched fraction(s) (e.g. the preferential crystallization). Therefore, a comparably large amount of energy and time is necessary to provide such an enriched solution.

It is the object of the present invention to provide an enhanced method capable of delivery of optically pure enantiomers and which addresses the above mentioned problems.

This object is achieved by a method according to claim 1, which method is for enantioseparation of a chiral system with compound formation comprising a pair of enantiomers, wherein the chiral system has an eutectic composition that exceeds already the required purity of the product to be achieved by the claimed method. The method comprises the steps of: placing the eutectic composition in the 3-phase region of the ternary phase diagram of chiral compound forming systems to achieve the establishment of the corresponding solid/liquid phase equilibria; and subsequently phase-separating the liquid and the solid phase formed by the placing step for obtaining the target enantiomer in the liquid phase.

This object is further achieved by a method according to claim 2, which method is for enantioseparation of a chiral system with compound formation comprising a pair of enantiomers. The method comprises the steps of: placing the chiral system to be processed, which is optically enriched by a target enantiomer in the 3-phase region of the ternary phase diagram of chiral compound forming systems to achieve the establishment of the solid/liquid phase equilibria; phase-separating the liquid and solid phase formed by the placing step; shifting the eutectic composition of the remaining liquid towards a lower eutectic composition, placing the overall composition in the outer 2-phase region; and performing crystallisation in the outer 2-phase region of the ternary phase diagram for obtaining the target enantiomer in the solid phase.

Figure 2:
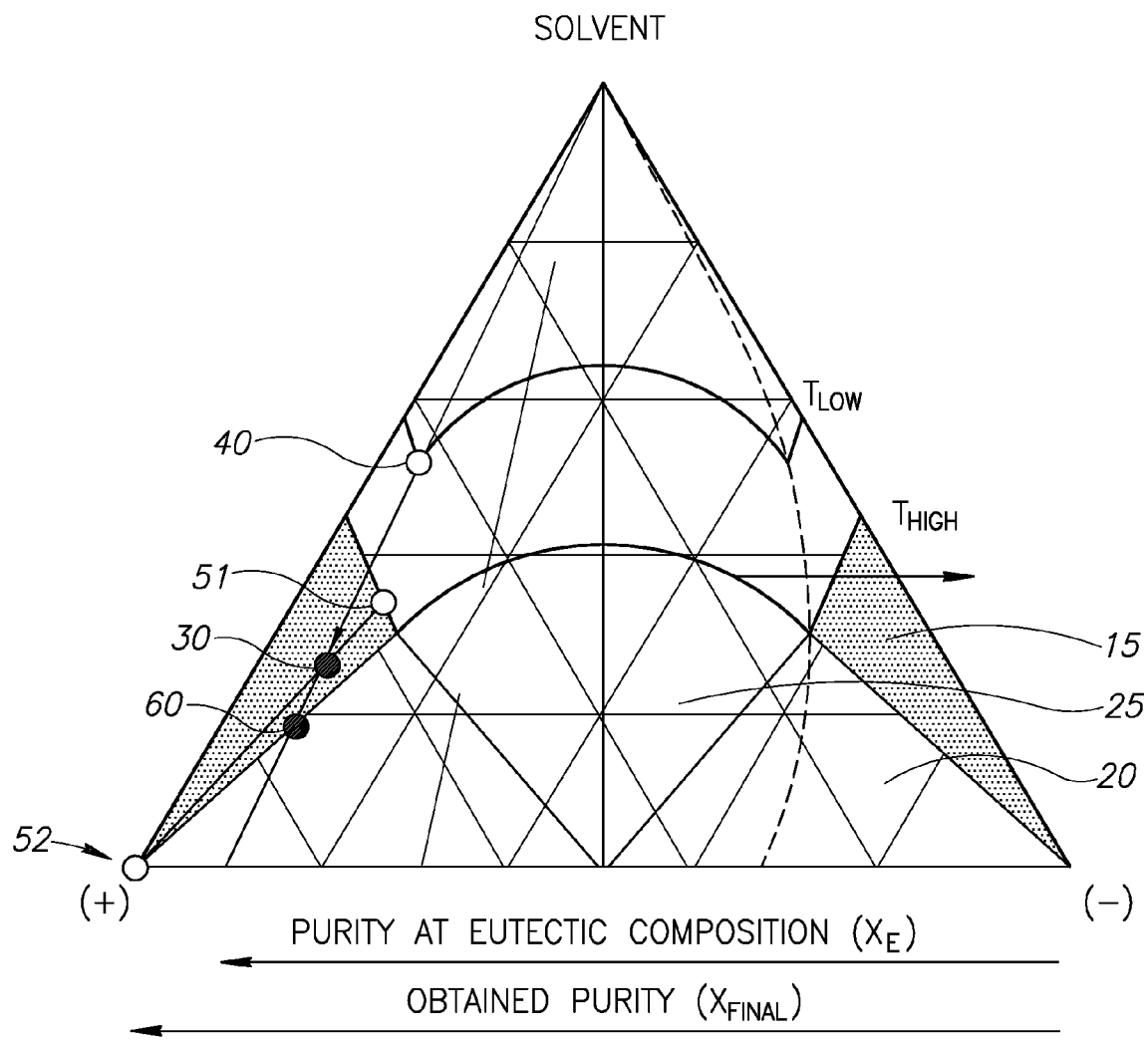

An adjustment of the concentration of the solution by e.g. partial evaporization leads to an overall composition, which is located in the outer 2-phase region (FIG. 2, 15). Selective crystallization can be performed in this 2-phase region of the ternary phase diagram in order to obtain the pure target enantiomer in the solid phase.

Advantageous developments are set out in the dependent claims.

The optically enriched chiral system to which the above-described method is applied can be an optically enriched liquid solution. In this case, the placing step can be performed by at least one of partial evaporation of the optically enriched solution, solvent change of the optically enriched solution, and addition of an antisolvent to the optically enriched solution.

In addition, the optically enriched chiral system to which the above-described method is applied can be an optically enriched solid mixture. In this case, the placing step can be performed by partial dissolution of the optically enriched solid mixture in a solvent.

Preferably, in order to start with a minimum of initial enrichment and to gain the highest yield, the placing step places the optically enriched chiral system onto the inner phase boundary of the 2- and 3-phase region of the ternary phase diagram of chiral compound forming systems to achieve the establishment of the solid/liquid phase equilibria.

It is possible to perform the phase-separating step by decanting the enriched liquid phase or by removing the solid phase by filtration or any other technique of solid/liquid phase separation.

The shifting step can be performed by a temperature change until the overall composition is located in the 2-phase region of the corresponding ternary phase diagram. Preferably, an additional evaporization step is therefore required.

The shifting step can also be performed by a (partial) exchange of the solvent until the overall composition is located in the 2-phase region of the corresponding ternary phase diagram. Preferably, an additional evaporization step is therefore required.

The shifting step can also be performed by a combination of a temperature change and a (partial) solvent exchange until the solution composition is located in the 2-phase region. Preferably, an additional evaporization step is therefore required.

Preferably, the shifting step shifts the remaining liquid onto the outer phase boundary between the 2- and the 3-phase region of the ternary phase diagram of the chiral compound forming system in order to obtain the highest yield.

Preferably, the crystallization is performed in the outer 2-phase region to gain pure target enantiomer in the crystalline phase.

The removed solid phase can be dried to dryness.

Figure 3:
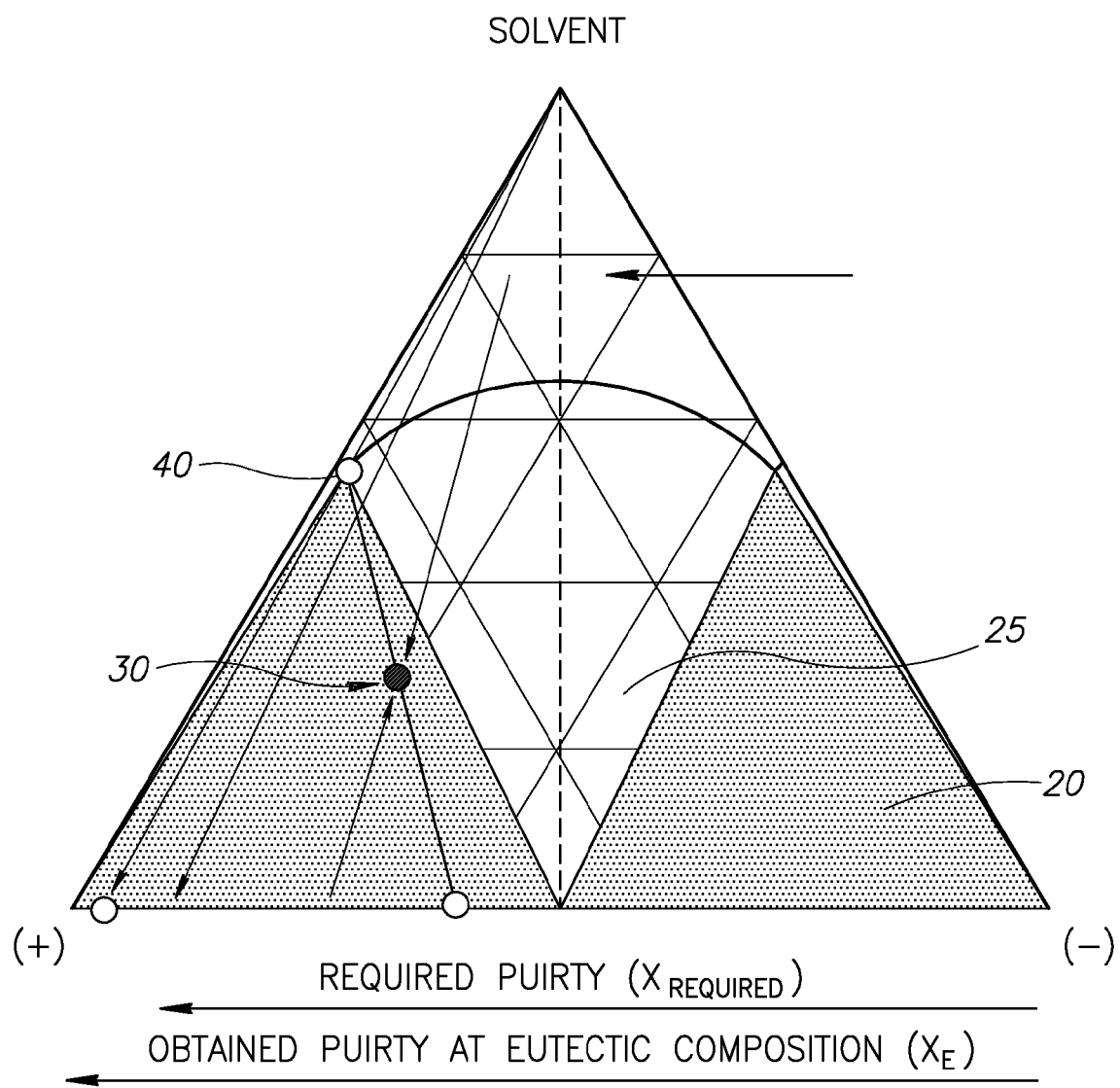

The previously described methods for enantioseparation of chiral systems with compound formation have the following advantages:
a) The initial enantiomeric enrichment can be very small, e.g. 1% excess is sufficient
b) Stable, thermodynamically dominated process i.e. method (equilibrium conditions apply)
c) Symmetric approach, each of the two enantiomers can be the target
d) Method can be operated in a continuous manner Hereinafter, the present invention will be further described in detail by reference to the appended drawings in which:

FIG. 1 shows a ternary phase diagram of a compound forming system. An optically enriched solution is placed within the 3-phase region and equilibration in step 1 of the method according to a first embodiment of the present invention is shown schematically;

FIG. 2 shows the ternary phase diagram of the same compound forming system in which partial evaporation of a solvent and enrichment of the target enantiomer in the solid phase in step 2 of the method according to the first embodiment of the present invention is shown schematically; and FIG. 3 shows a ternary phase diagram of a compound forming system in which the method according to a second embodiment of the present invention is shown schematically.

In the following, a separation scheme is introduced, which aims to yield pure enantiomers from an optically enriched solution (originating e.g. from partial chromatographic resolution of a racemate, selective membranes or partial asymmetric synthesis). The knowledge of the related ternary phase diagram consisting of a pair of enantiomers and a solvent, is the key for the separation method described below. This method is suitable for compound forming systems, which represent the majority (more than 90%) of all known systems of enantiomers. It is sufficient for this method, when the initial solution is only slightly optically enriched by the target enantiomer, i.e. L- or D-entantiomer or (S)- or (R)-entantiomer, respectively.

First Embodiment

It is known from investigations described in the literature and own experimental results that the eutectic composition in the chiral system (intersection of the solubility isotherms of the enantiomers and the racemic compound) can be shifted either by temperature change or variation of the solvent (mixture). In FIGS. 1 and 2, a shift towards a lower eutectic composition $x_E$ between a lower temperature $T_{low}$ and a higher temperature $T_{high}$ is shown (dashed black line). This variation is exploited to enter the 2-phase region 15 of the ternary phase diagram in step 2 (shaded area in FIG. 2)

Step 1:
Either partial evaporation of an optically enriched solution or partial dissolution of an optically enriched solid mixture (e.g. arrows pointing towards dot 30 in FIG. 1) in order to place the resulting composition of the solution within the 3-phase region 20 of the typical phase diagram of chiral compound forming systems (first substep: placing). Upon equilibration, the target enantiomer accumulates in the liquid phase (FIG. 1, dot 40, $x_E$) due to the establishment of the solid/liquid phase equilibria (tie line linking dots 40, 41 in FIG. 1). The optimal yield is obtained in the liquid phase, if the overall composition is located anywhere at the inner phase boundary between the 2- and the 3-phase region (FIG. 1, tie line linking dots 40, 42, e.g. at 43).

Alternatively, a solvent change or the addition of an anti-solvent to the optically enriched initial solution enables to enter the 3-phase region 20 (of the corresponding ternary phase diagram).

Step 2:
At first, a phase separation is done of the liquid and the solid phase formed after step 1 (second substep: phase-separating). Therefore, the enriched liquid phase (dot 40 in FIG. 1 and FIG. 2) is either decanted or the corresponding solid phase (dot 41 in FIG. 1) is removed by filtration. The remaining mother liquor is concentrated by partial evaporation of the solvent until the composition is located in the 2-phase-region 15 at the corresponding higher temperature $T_{high}$ (e.g. composition of dot 30 in FIG. 2) (third substep: shifting). Now a classical crystallization process in this region of the ternary phase diagram yields directly the target enantiomer in the solid phase (dot 52 in the lower left corner of FIG. 2, theoretical value of $x_{final}$=100%) (fourth substep: crystallising).

The maximum yield would be obtained if the evaporation stops on the outer phase boundary (dot 60 in FIG. 2).

While a shift of the eutectic composition towards larger $x_E$ from $T_{low}$ to $T_{high}$ might be possible, too, the shown direction (FIGS. 1, 2) was found more frequently up to now. In case of a shift of the eutectic composition towards larger $x_E$ for higher temperatures, one would enrich the solution in step 1 at $T_{high}$ and subsequently decant the liquid phase or remove the solid phase by filtration. In step 2, the solution is already located in the 2-phase region 15 (FIG. 2) at $T_{low}$. Then again, classical crystallization yields pure enantiomers in the same manner.

It is observed from own experiments that a shift of the eutectic composition can occur due to a change of the solvent, as well. Thus, instead of a temperature change, also a change of the solvent (or a combination of both) can be applied to enter the 2-phase region 15.

Experimental verification of the case described in FIGS. 1 and 2 is provided in the following.

Example of Separation of Methionine Enantiomers

The following example for the method described in the first embodiment is given for better understanding of the present invention only and does not limit the above-described method to the given values or specific method steps used. The person skilled in the art will acknowledge that the following steps can equally be executed according to all of the above described principles.

As an illustrating example, to obtain optically pure L-enantiomer from a slightly enriched aqueous solution, the following mixture was subjected to the previously described 2-step method:
L-/DL-methionine (Sigma-Aldrich, purity: DL 99%; L 98%)
deionized water
Required Thermodynamic Data for Process i.e. Method Design (Own Data)

| Temperature [K] | Optical purity at eutectic composition: $\frac{L}{L+D}$ [%] | Solubility at eutectic composition [wt %] |
| --- | --- | --- |
| 274.15 | 94.18 | '3.83 |
| 333.15 | 85.98 | '9.38 |

Experimental Procedure:
Step 1:

A physical mixture of crystals of the racemic compound (DL-methionine) and the L-enantiomer (387.44 g and 59.69 g) were added to a 2000 ml reactor vessel. The composition was chosen to represent a possible output of a previous partial enrichment step via another reaction or separation step. This initial mixture was only slightly enriched by the target enantiomer (optical purity 56.7%). 1000 g of water were added and the slurry was properly agitated and kept at isothermal conditions at 274.15 K for 4 days to ensure thermodynamic solid/liquid phase equilibrium. The duration can probably be shortened much in terms of process i.e. method optimization. Analysis by means of chiral chromatography yielded an optical purity in the liquid phase of 93.8% L-enantiomer after this period.

Step 2:

Subsequently the solid phase was filtrated off and the liquid phase was decanted to another reactor vessel and heated to a temperature of 333.15 K.

A fraction of the solvent was evaporated by means of vacuum distillation at 190 mbar aiming to enter the 2-phase area defined by the solubility isotherm at this temperature. The eutectic composition of the methionine enantiomers in water at a temperature of 333.15 K was experimentally determined earlier to 86% optical purity. During the partial removal of the solvent and the generation of supersaturation spontaneous nucleation occurred and the L-enantiomer crystallized with 100% optical purity within the reactor vessel. The final crystalline product mass after solvent removal exhibited an optical purity of 98.6%. The maximal theoretical yield for this system under the conditions of the experiment, governed by the thermo-dynamic equilibrium, is obtained at the phase boundary between the 2- and the 3-phase area (~54% for this case). For this experimental run, the second process step was stopped clearly above the inner phase boundary. An overall yield of 33% (19.72 g product L-methionine/59.69 g) was obtained which was also diminished by product losses during the two filtration steps, which leaves potential for process improvements. By complete avoidance of crystallization of the mother liquor onto the crystalline product, 100% purity can be achieved. Promising techniques for this issue are already commercially available and not part of the present application. The mother liquor, which was filtrated off, showed an optical purity of 86.0%. That makes this phase suitable to be used in combination with new feed material in order to enhance further the method efficiency. Since this solution has to be diluted again for reuse in the above-described step 1, an even less optical enriched output stream from a chromatographic separation could be used for mixing in favourable synergistic manner.

To sum up, optically pure L-enantiomer was obtained from a slightly enriched solution (56.7%) by two subsequent crystallization steps. Upon knowledge of the underlying phase equilibria, only a balance to determine the amount of removed solvent and a thermocouple with a thermostat was needed to track the enrichment trajectories.

Second Embodiment

Next a second embodiment of the method according to the present invention is described by reference to FIG. 3.

For certain systems of enantiomers it is possible to partially skip step 2 described in the first embodiment. Just the second substep: phase-separation is required. This is the case when the eutectic composition exceeds already the required purity of the product ($x_E > x_{purity}$). The liquid phase can be decanted or the crystalline phase can be removed by filtration (second to substep: phase-separation). The target enantiomer is present in the crystalline product after evaporation of the solvent from the liquid phase.

Experimental verification of the case described in FIG. 3 is provided in the following.

(Example of Separation of Serine Enantiomers)

The following example for the method described in the second embodiment is given for better understanding of the present invention only and does not limit the above-described method to the given values or specific method steps used. The person skilled in the art will acknowledge that the following steps can equally be executed according to all of the above described principles.

As an illustrating example, to obtain optically pure L-enantiomer from a slightly enriched aqueous solution, the following mixture was subjected to the previously described method in which step 2 of the first embodiment was skipped partially:

L-/DL-Serine (Sigma-Aldrich, purity: DL 99%; L 99%)
deionized water

Required Thermodynamic Data for Process i.e. Method Design (Own Data)

| Temperature [K] | Optical purity at eutectic composition: $\frac{L}{L+D}$ [%] | Solubility at eutectic composition [wt %] |
| --- | --- | --- |
| 313.15 | 99.4 | ' 2.46 |

Experimental Procedure:
Step 1:

A physical mixture of crystals of the racemic compound and the L-enantiomer (53.60 g and 13.19 g) were added to a 300 ml vessel. The mixture was enriched by the target enantiomer (optical purity 59.9%). A solvent consisting of 81.01 g water and 121.52 g methanol (60:40 wt/wt) was added and the slurry was properly agitated and kept at isothermal conditions at 313.15 K for 2 days to ensure thermodynamic solid/liquid phase equilibrium. The overall composition was chosen to represent an output of a previous partial enrichment step by chiral chromatography e.g. on a SMB system. Analysis by means of chiral chromatography yielded an optical purity in the liquid phase of 99.4% L-enantiomer after equilibration.

The liquid phase was removed through a filter and dried to dryness. The generated crystals were of 99.4% optical purity.

To sum up, L-serine was optically purified to 99.4% from a mixture of 59.9% optical purity. In principle, only the first step became necessary to conduct, since the eutectic composition in solution provides sufficient purity. From step 2 just the phase separation step was required.

Other

The previously described execution possibilities of the different substeps of steps 1 and 2 of the method for enantioseparation of chiral systems with compound formation can be conducted both separately as well as in all possible combinations of the previously mentioned method steps.

For example, it is possible to perform the placing step by partial evaporation of the optically enriched solution wherein a solvent change of the optically enriched solution is performed beforehand. Further, performing the placing step by addition of an antisolvent to the optically enriched solution and partial evaporation of the optically enriched solution is possible, too.

Moreover, the phase-separating step can be performed by any of the known techniques for solid/liquid phase separation, e.g. by decanting the enriched liquid phase and removing the solid phase by filtration.

In addition, the shifting step to locate the chiral system in the 2-phase region can be performed by a combination of a temperature change in the ternary system and a (partial) change of the solvent or just one of the techniques.

Other possible combinations of the above steps and sub-steps will be apparent to those skilled in the art.

LIST OF REFERENCE SIGNS 5 1-phase region
15 outer 2-phase region of the ternary phase diagram of chiral compound forming systems
20 3-phase region of the ternary phase diagram of chiral compound forming systems
25 inner 2-phase region of the ternary phase diagram of chiral compound forming systems
30 possible placement of solution composition within step 1
40 liquid phase composition after equilibration within step 1
41 sub optimal solid phase composition after equilibration within step 1
42 solid phase composition after equilibration within step 1 (ideal case)
43 optimal overall composition after equilibration within step 1 in terms of maximum yield
50 possible overall composition after partial evaporization and equilibration within step 2
51 possible liquid phase composition after partial evaporization and equilibration within step 2
52 solid phase composition after partial evaporization and equilibration within step 2
60 optimal overall composition after partial evaporization and equilibration within step 2 in terms of maximum yield
$x_E$ purity at eutectic composition
$x_{final}$ obtained purity
$x_{required}$ required purity
$T_{low}$ lower temperature
$T_{high}$ higher temperature

The invention claimed is:

1. A method for enantioseparation of a chiral system with racemic compound formation comprising a pair of enantiomers, the method comprising the steps of:
    placing the chiral system to be processed, which is optically enriched by a target enantiomer, in the 3-phase region of the ternary phase diagram of chiral compound forming systems to achieve the establishment of the solid/liquid phase equilibria;
    phase-separating the liquid and solid phase formed by the placing step;
    shifting the eutectic composition of the remaining liquid towards a lower eutectic composition (xE) closer to the racemic composition to achieve a new ternary phase diagram;
    placing the overall composition in the outer 2-phase region of the new ternary phase diagram; and
    performing crystallisation in the outer 2-phase region of this new ternary phase diagram for obtaining the target enantiomer in the solid phase.

2. The method according to claim 1, wherein the shifting step is performed by a temperature change until the overall composition is located in the 2-phase region of the corresponding ternary phase diagram.

3. The method according to claim 1, wherein the shifting step is performed by a solvent change until the overall composition is located in the 2-phase region of the corresponding ternary phase diagram.

4. The method according to claim 2, wherein the shifting step shifts the remaining liquid onto the outer phase boundary between the 2- and the 3-phase region.

5. The method according to claim 1, wherein the removed solid phase is dried to dryness.

6. The method according to claim 1, wherein the chiral system is an optically enriched liquid solution.

7. The method according to claim 6, wherein the placing step is performed by partial evaporation of the optically enriched liquid solution.

8. The method according to claim 6, wherein the placing step is performed by a solvent change of the optically enriched liquid solution.

9. The method according to claim 6, wherein the placing step is performed by addition of an antisolvent to the optically enriched liquid solution.

10. The method according to claim 1, wherein the chiral system is an optically enriched solid mixture and wherein the placing step is performed by partial dissolution of the optically enriched solid mixture in a solvent.

11. The method according to claim 1, wherein the placing step causes the optically enriched liquid solution to be placed onto a inner phase boundary of the 2- and 3-phase region of the ternary phase diagram of chiral compound forming systems to achieve the establishment of the equilibrium of the solid phase and the liquid phase.

12. The method according to claim 1, wherein the phase-separating step is performed by decanting the liquid phase.

13. The method according to claim 1, wherein the phase-separating step is performed by removing the solid phase by filtration.

14. The method according to claim 13, wherein the removed solid phase is dried.

15. The method according to claim 12, wherein the removed solid phase is dried.

16. The method according to claim 1, wherein the final purity is higher than a purity of the eutectic composition of the new ternary phase diagram.

17. The method according to claim 1, wherein the chiral system has an eutectic composition that exceeds already the required purity ($x_{required}$) of the product to be achieved; further comprising the steps of
    not shifting the eutectic composition of the remaining liquid and
    obtaining the target enantiomer directly in the liquid phase after phase-separating the liquid and the solid phase formed by the step of placing the chiral system in the 3-phase region of the ternary phase diagram.

* * * * *